(12) United States Patent
Lee et al.

(10) Patent No.: US 12,007,302 B2
(45) Date of Patent: Jun. 11, 2024

(54) GAS SENSOR

(71) Applicant: HYUNDAI KEFICO CORPORATION, Gyeonggi-do (KR)

(72) Inventors: Seung Tae Lee, Gyeonggi-do (KR); Dae Gun Lee, Gyeonggi-do (KR); Kyeong Hyeon Kim, Anyang Gyeonggi-do (KR)

(73) Assignee: Hyundai Kefico Corporation, Gyeonggi-do (KR)

( * ) Notice: Subject to any disclaimer, the term of this patent is extended or adjusted under 35 U.S.C. 154(b) by 323 days.

(21) Appl. No.: 17/502,011

(22) Filed: Oct. 14, 2021

(65) Prior Publication Data
US 2022/0113212 A1    Apr. 14, 2022

(30) Foreign Application Priority Data

Oct. 14, 2020 (KR) .......................... 10-2020-0132714
Aug. 23, 2021 (KR) .......................... 10-2021-0110608

(51) Int. Cl.
*G01M 3/04* (2006.01)
*G01N 1/22* (2006.01)

(52) U.S. Cl.
CPC ............. *G01M 3/04* (2013.01); *G01N 1/2273* (2013.01)

(58) Field of Classification Search
CPC ................. G01D 11/245; G01D 11/24; G01N 2001/2276; G01N 1/2273; G01N 33/0004; G01N 2001/2288; G01N 27/4045; G01N 33/0031
See application file for complete search history.

(56) References Cited

U.S. PATENT DOCUMENTS 4,080,832 A * 3/1978 Moody ................ G01N 1/2273
                                                    73/864.34
4,769,122 A * 9/1988 Marrese ............. G01N 27/4045
                                                    204/408
(Continued)

FOREIGN PATENT DOCUMENTS

JP            2000187014 A  *  7/2000
JP            2010-122099 A     6/2010
(Continued)

OTHER PUBLICATIONS

Espacenet Machine Translation of JP 2000187014 A Originally Published On Jul. 4, 2000. (Year: 2000).*
(Continued)

*Primary Examiner* — Kristina M Deherrera
*Assistant Examiner* — Mark A Shabman
(74) *Attorney, Agent, or Firm* — Fox Rothschild LLP

(57) ABSTRACT

A gas sensor includes a housing having an open portion at one side of the housing, a circuit board securely provided inside the housing, the circuit board defining a gas sensing space in the housing that communicates with the open portion of the housing, the circuit board having a sensing element located in the gas sensing space and configured to sense a specific gas, a holder provided inside the gas sensing space, and fixed to the housing, the holder having a through hole communicating with the open portion of the housing, and a filter provided inside the gas sensing space, and coupled to the holder or the housing so as to cover the through hole or the open portion.

19 Claims, 13 Drawing Sheets

(56) References Cited

U.S. PATENT DOCUMENTS

| | | | | |
|---|---|---|---|---|
| 5,338,429 A * | 8/1994 | Jolson | ............... | G01N 27/4045 204/415 |
| 6,351,982 B1 * | 3/2002 | Tindall | ............... | G01N 27/16 73/23.31 |
| 7,479,255 B2 * | 1/2009 | Otani | ............... | H01M 8/0662 436/159 |
| 7,608,177 B2 * | 10/2009 | Nauber | ............... | G01N 27/404 204/411 |
| 7,802,472 B1 * | 9/2010 | Richer | ............... | G01D 11/245 73/431 |
| 8,318,525 B2 * | 11/2012 | Davies | ............... | G01N 27/16 73/23.31 |
| 8,702,935 B2 * | 4/2014 | Davis | ............... | G01N 27/40 156/60 |
| D760,102 S * | 6/2016 | Frandsen | ............... | D10/81 |
| 9,709,425 B2 * | 7/2017 | Matsui | ............... | G01D 11/24 |
| 10,324,024 B2 * | 6/2019 | Pavey | ............... | G01N 21/783 |
| 10,605,686 B2 * | 3/2020 | Pusheck | ............... | B60R 11/00 |
| 10,739,268 B2 * | 8/2020 | Bieri | ............... | G01N 15/0625 |
| 10,983,085 B2 * | 4/2021 | Matsukura | ............... | G01N 27/4074 |
| 11,187,670 B2 * | 11/2021 | Liu | ............... | G01N 27/404 |
| 11,300,549 B2 * | 4/2022 | Micalizzi | ............... | H04Q 9/00 |
| 11,360,002 B2 * | 6/2022 | Miller-Lionberg | ............... | G01N 15/0255 |
| 11,513,091 B2 * | 11/2022 | Potasek | ............... | G01N 33/0044 |
| 11,674,900 B2 * | 6/2023 | Henderson | ............... | G01N 21/3504 73/23.3 |
| 2008/0145722 A1 * | 6/2008 | Coignet | ............... | G01N 33/005 429/432 |
| 2009/0267357 A1 * | 10/2009 | Hall | ............... | E05B 63/125 292/99 |
| 2011/0088454 A1 * | 4/2011 | Seeck | ............... | G01N 1/2208 73/29.01 |
| 2014/0076026 A1 * | 3/2014 | Starling | ............... | G01N 27/00 73/29.02 |
| 2015/0143901 A1 * | 5/2015 | Matsui | ............... | G01L 19/148 73/431 |
| 2015/0362451 A1 * | 12/2015 | Hunziker | ............... | G01N 27/26 73/31.06 |
| 2020/0309647 A1 * | 10/2020 | Smedsrud | ............ | G01N 1/2205 |
| 2020/0400597 A1 * | 12/2020 | Barbul | ............... | G01N 27/028 |
| 2021/0172899 A1 * | 6/2021 | Xiao | ............... | G01N 33/004 |
| 2021/0247368 A1 * | 8/2021 | Doshi | ............... | G01N 27/4075 |
| 2022/0018819 A1 * | 1/2022 | Tanabe | ............... | G01N 27/128 |

FOREIGN PATENT DOCUMENTS

| | | | | |
|---|---|---|---|---|
| JP | 4683537 B2 | 5/2011 | | |
| JP | 2016-24797 A | 2/2016 | | |
| JP | 2017-122616 A | 7/2017 | | |
| KR | 100645575 B1 | 11/2006 | | |
| KR | 20110053560 A * | 5/2011 | ......... | G01N 27/404 |
| KR | 102012473 B1 | 8/2019 | | |

OTHER PUBLICATIONS

Espacenet Machine Translation of KR 20110053560 A Originally Published On May 24, 2011. (Year: 2011).*

Office Action dated Feb. 28, 2023 in corresponding Korean Application No. 10-2021-0110608.

* cited by examiner

GAS SENSOR

CROSS REFERENCE TO RELATED APPLICATION

The present application claims under 35 U.S.C. § 119(a) the benefit of Korean Patent Application No. 10-2020-0132714, filed Oct. 14, 2020, and Korean Patent Application No. 10-2021-0110608, filed Aug. 23, 2021, the entire contents of which are incorporated by reference herein.

BACKGROUND

(a) Technical Field

The present disclosure relates to a gas sensor, more particularly, to a gas sensor configured to sense leakage of a specific gas such as hydrogen.

(b) Description of the Related Art

There is a risk of explosion due to leakage when using flammable hydrogen gas. Therefore, when using hydrogen gas, a technique for sensing hydrogen gas leakage is essential for preventing an accident due to hydrogen gas leakage.

In general, hydrogen gas is used in various fields from semiconductor thin film processing to automobile fuel cells and rocket fuels in the aerospace industry as well as hydrogen fuel cells, and is gradually expanding its range of uses due to technological development.

A gas sensor configured to sense hydrogen gas includes a hydrogen sensing unit that senses hydrogen gas leakage using various hydrogen gas sensing methods, such as a catalytic combustion type method using a catalyst, a semiconductor type method using a semiconductor oxide, and an electrolyte sensor using an electrolyte that reacts with hydrogen.

For example, a conventional gas sensor typically has a sensing space for introducing gas into an inside of the gas sensor to sense a specific gas, and a technique for fixing a filter to an open portion of the sensing space is applied to the gas sensor. However, the conventional gas sensor has a problem in that it is difficult to prevent foreign substances such as moisture from being introduced into a coupling portion in which the filter and the housing are coupled to each other.

The foregoing is intended merely to aid in the understanding of the background of the present disclosure, and is not intended to mean that the present disclosure falls within the purview of the related art that is already known to those skilled in the art.

SUMMARY

Accordingly, the present disclosure provides a gas sensor configured to prevent foreign substances from being introduced into a gas sensing space.

In order to achieve the above objective, according to one aspect of the present disclosure, there is provided a gas sensor including: a housing having an open portion at one side of the housing; a circuit board securely provided inside the housing, the circuit board defining a gas sensing space in the housing that communicates with the open portion of the housing, the circuit board having a sensing element located in the gas sensing space and configured to sense a specific gas; a holder provided inside the gas sensing space, and fixed to the housing, the holder having a through hole communicating with the open portion of the housing; and a filter provided inside the gas sensing space, and coupled to the holder or the housing so as to cover the through hole or the open portion.

The housing may include a support that may be extended to protrude from a bottom surface at a periphery of the open portion of the housing toward the circuit board, and the holder may be coupled to the support while being spaced apart from the bottom surface at the periphery of the open portion of the housing toward the circuit board.

The holder may be integrally coupled to the support by being fused thereto by ultrasonic waves, lasers, vibration, or heat.

The holder may be expanded outward more than the support, the holder having an insertion groove at a portion between an outer end and an inner end of the holder surrounding the through hole, and the support may be coupled to the holder while being located between the outer end and the inner end of the holder and being inserted in the insertion groove.

The holder may have protrusions, the protrusions being formed on a plurality of locations on the outer end or the inner end of the holder and protruding toward the insertion groove and being circumferentially spaced apart from each other, and the support may be fixed at a location inside the insertion groove by being in contact with the protrusions.

The holder may have a curved surface as the inner end of the holder is gradually extended inward.

An adhesive may be applied on a portion between the holder and the bottom surface in the housing that may be spaced apart from each other, and the holder may be integrally coupled to the housing by the adhesive.

The circuit board may be coupled to the housing while facing the open portion of the housing, so that the gas sensing space may be maintained in airtight from an inside space of the housing.

The housing may have a seating groove located outside the gas sensing space and depressed in a direction that may be spaced apart from the circuit board, the housing further including an elastic body located between the housing and the circuit board and disposed in the seating groove.

The filter may be expanded outward more than the through hole to cover the through hole and be coupled to the holder at a side opposite to the open portion of the housing.

The filter may be integrally coupled to the holder or the housing by being fused thereto by ultrasonic waves, lasers, vibration, or heat while being spaced apart from the circuit board.

A guide member may be fixed to the housing, the guide member being extended in a direction perpendicular to a penetrating direction of the through hole to cover the through hole, at the open portion, in the penetrating direction of the through hole.

The guide member may have a circular shape with a radius that may be equal to or longer than a distance between the guide member and the through hole and be shorter than or equal to a distance between the guide member and the filter.

The filter may be provided between the housing and the holder and covers both the open portion of the housing and the through hole at the same time, the filter defining the gas sensing space while being spaced apart from the circuit board.

The housing may include a support that may be extended to protrude from a bottom surface at a periphery of the open portion toward the circuit board, and the holder may be fixed to the housing while being inserted in the support.

The holder may be extended outward such that, a part of or an entire outer end of the holder may be extended outward more than an inner circumferential surface of the support, the holder being integrally coupled to the support by a forced insertion manner.

The holder may have an inclined protrusion, the inclined protrusion protruding outward from at least one location on an outer end of the holder and being configured to be deformed while being inserted into the support.

The inclined protrusion may be inclined such that a height of the inclined protrusion may be lowered as the inclined protrusion goes in an inserted direction into the support, or be inclined such that a width of the inclined protrusion may narrow as the inclined protrusion is extended outward.

The support may be configured to be thermally deformed while accommodating the holder therein and thus be integrally coupled to the holder.

The support may be extended higher than a height of the holder, and as an end at the circuit board side of the support is directed toward the circuit board, an inner circumferential surface of the support may be depressed to be inclined outward, so that the support may be thermally deformed inward.

According to the present disclosure, the gas sensor has the holder and the filter that are located inside the gas sensing space. Therefore, the gas sensor can prevent foreign substances filtered by the filter from penetrating into the gas sensing space.

Furthermore, leakage of gas introduced into the gas sensing space can be prevented by coupling the housing to the circuit board of the gas sensor.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE DISCLOSURE

Figure 1:
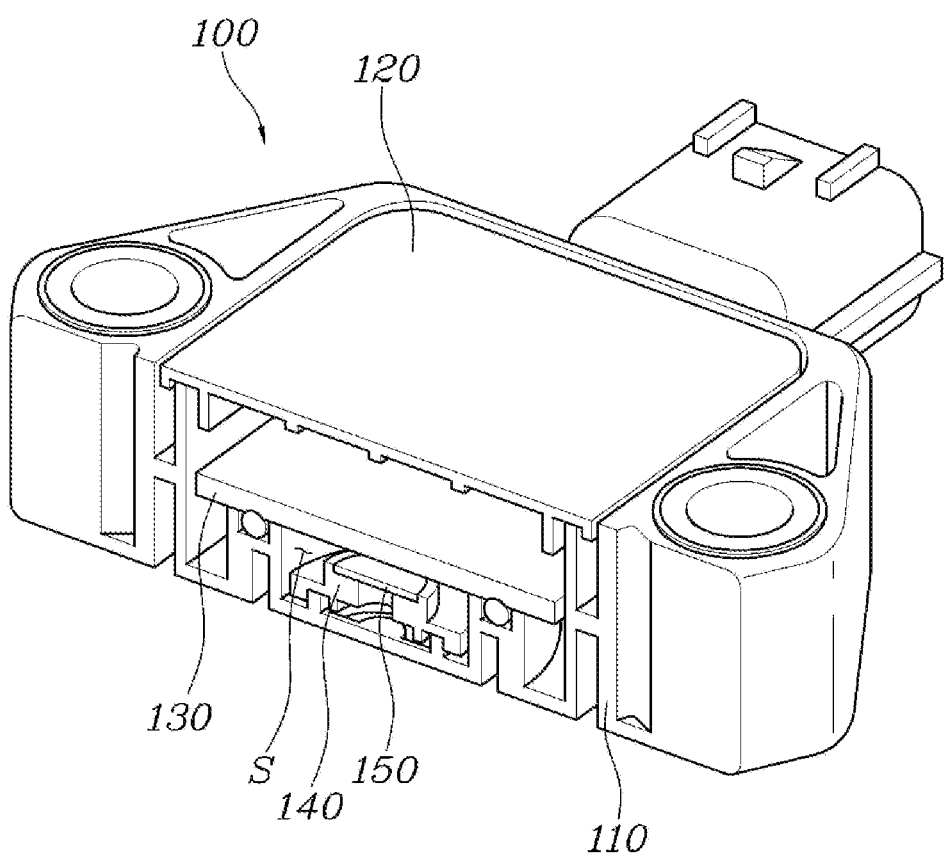
FIG. 1 is a perspective view showing a gas sensor in a cut away state according to an embodiment of the present disclosure.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

In the following description, the structural or functional description specified to exemplary embodiments according to the concept of the present disclosure is intended to describe the exemplary embodiments, so it should be understood that the present disclosure may be variously embodied, without being limited to the exemplary embodiments.

Embodiments described herein may be changed in various ways and various shapes, so specific embodiments are shown in the drawings and will be described in detail in this specification. However, it should be understood that the exemplary embodiments according to the concept of the present disclosure are not limited to the embodiments which will be described hereinbelow with reference to the accompanying drawings, but all of modifications, equivalents, and substitutions are included in the scope and spirit of the disclosure.

It will be understood that, although the terms first and/or second, etc. may be used herein to describe various elements, these elements should not be limited by these terms. These terms are only used to distinguish one element, from another element. For instance, a first element discussed below could be termed a second element without departing from the teachings of the present disclosure. Similarly, the second element could also be termed the first element.

It is to be understood that when one element is referred to as being "connected to" or "coupled to" another element, it may be connected directly to or coupled directly to another element or be connected to or coupled to another element, having the other element intervening therebetween. On the other hand, it is to be understood that when one element is referred to as being "connected directly to" or "coupled directly to" another element, it may be connected to or coupled to another element without the other element intervening therebetween. Further, the terms used herein to describe a relationship between elements, that is, "between", "directly between", "adjacent" or "directly adjacent" should be construed in the same manner.

The terminology used herein is for the purpose of describing particular embodiments only and is not intended to limit the present disclosure. Singular forms are intended to include plural forms unless the context clearly indicates otherwise.

Unless otherwise defined, all terms including technical and scientific terms used herein have the same meaning as commonly understood by those skilled in the art to which the present disclosure belongs. It must be understood that the terms defined by the dictionary are identical with the meanings within the context of the related art, and they should not be ideally or excessively formally defined unless the context clearly dictates otherwise.

Hereinbelow, preferred embodiments of the present disclosure will be described in detail with reference to accompanying drawings. The same reference numerals will be used throughout the drawings to refer to the same or like elements or parts.

Figure 2:
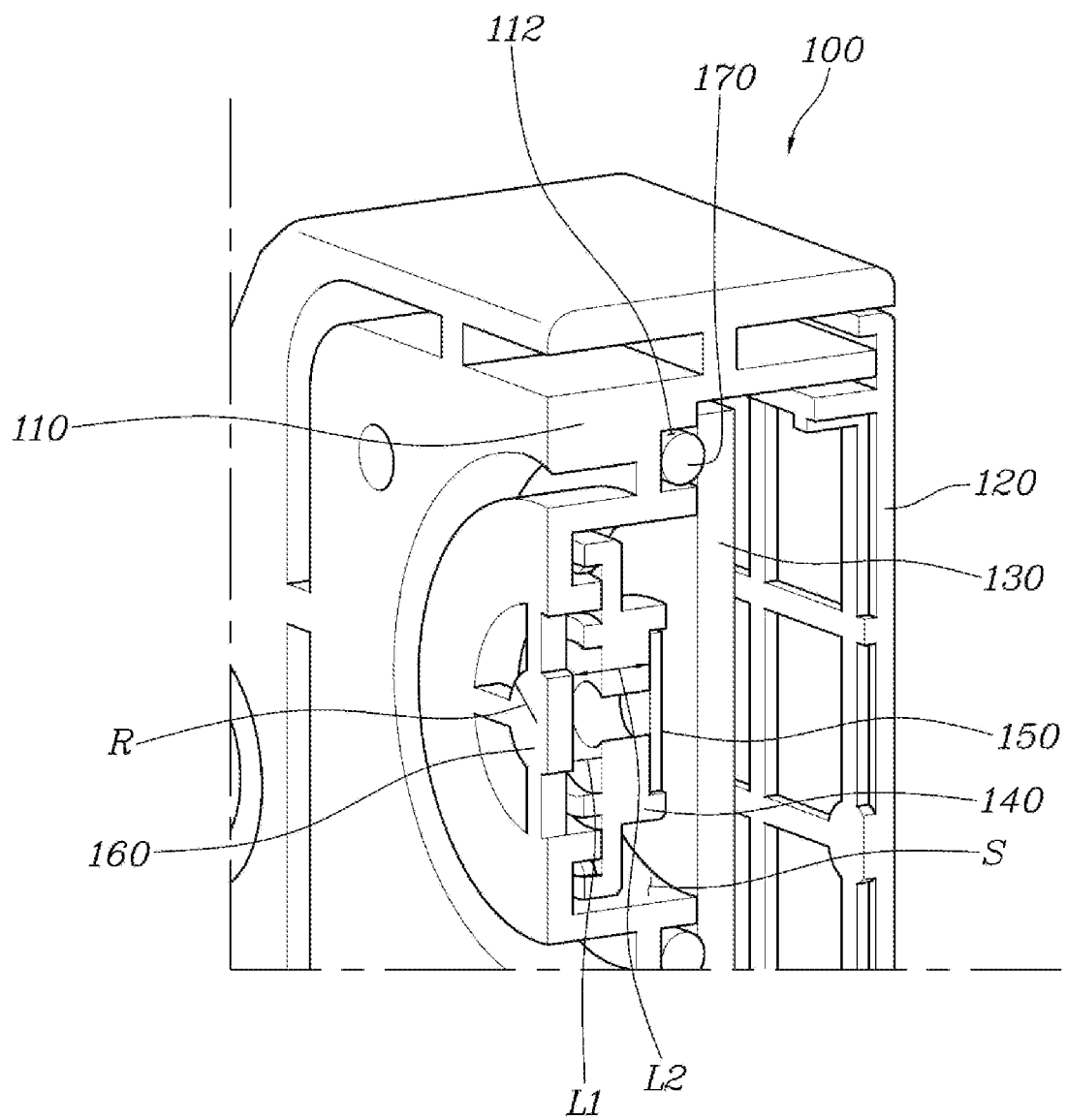
FIG. 2 is an enlarged view showing the gas sensor shown in FIG. 1.
Figure 3:
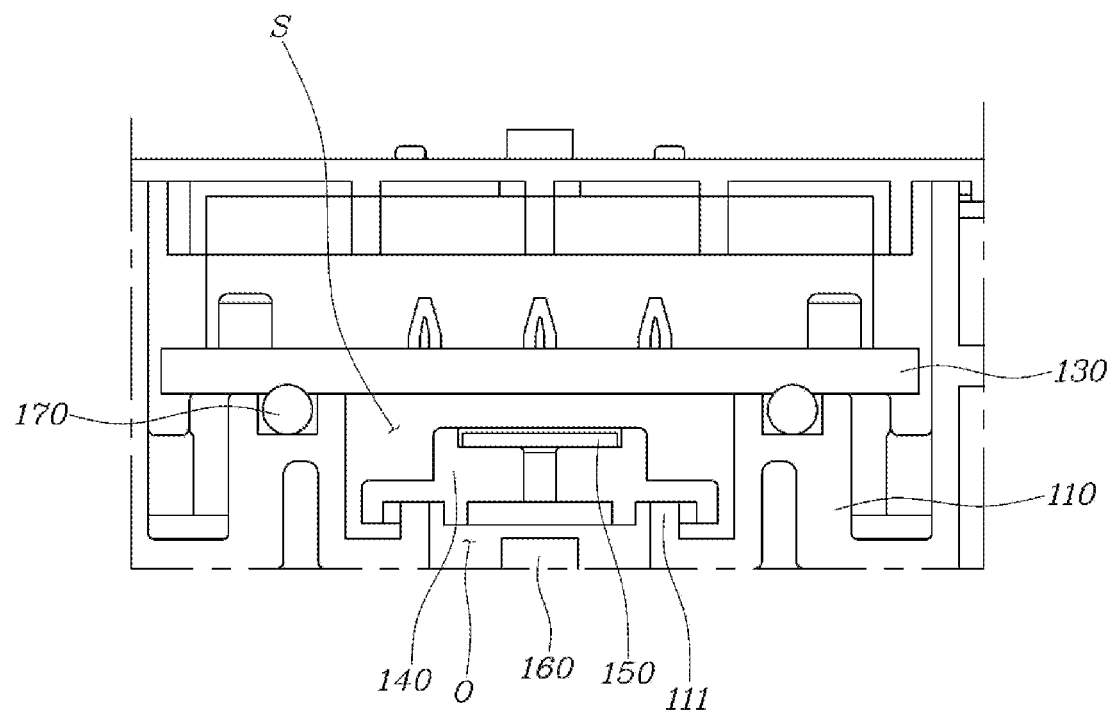
FIG. 3 is a sectional view showing the gas sensor according to the embodiment of the present disclosure.

FIG. 1 is a perspective view showing a gas sensor in a cut away state according to an embodiment of the present disclosure. FIG. 2 is an enlarged view showing the gas sensor shown in FIG. 1. FIG. 3 is a sectional view showing the gas sensor according to the embodiment of the present disclosure.

Referring to FIGS. 1 to 3, the gas sensor 100 according to the embodiment of the present disclosure includes: a housing 110 having an open portion O at one side of the housing 110; a circuit board 130 securely provided inside the housing 110, the circuit board 130 defining a gas sensing space S in the housing 110 that communicates with the open portion O of the housing 110, the circuit board 130 including a sensing element that is located in the gas sensing space S and is configured to sense a specific gas; a holder 140 provided inside the gas sensing space S and fixed to the housing 110 while covering the open portion O, the holder 140 having a through hole communicating with the open portion O; and a filter 150 provided inside the gas sensing space S and coupled to the holder 140 so as to cover the through hole.

The circuit board 130, a connector, etc. may be mounted in the housing 110. The open portion O through which gas flows may be provided at a first side of the housing 110. A cover 120 may be coupled to a second side of the housing 110 to provide an inside space of the housing 110.

The gas sensing space S may be separately partitioned in the inside space of the housing 110. The gas sensing space S may be defined by the circuit board 130 located in the housing 110. The gas sensing space S may be surrounded by the housing 110 and the circuit board 130.

The gas sensing space S may communicate with the open portion O of the housing 110. Therefore, the gas sensing space S may be open to the outside of the gas sensor by the open portion O of the housing 110.

The circuit board 130 may be a printed circuit board (PCB) 130 as the embodiment, and may provide one surface covering the gas sensing space S by being expanded in a planar direction. The sensing element may be provided in the circuit board 130. The sensing element may be located inside the gas sensing space S and sense a specific gas.

As the embodiment, the sensing element may sense hydrogen gas. A catalytic combustion type, a semiconductor type using a semiconductor oxide, an electrolyte type using an electrolyte that reacts to hydrogen, or a heat conduction type using thermal conductivity may be applied as a sensing principle.

The circuit board 130 may determine a specific gas by using a feature sensed by the sensing element according to the sensing principle through signal-processing.

The holder 140 may be located inside the gas sensing space S and may be coupled to the housing 110. The holder 140 may be expanded in the planar direction so as to cover the open portion O.

The holder 140 may have the through hole extended toward the gas sensing space S. The through hole may communicate with the open portion O. The through hole may be formed smaller than the open portion O.

The filter 150 may be formed of a membrane as the embodiment. The filter 150 may filter foreign substances such as moisture flowing into the gas sensing space S. Furthermore, the filter 150 may be located inside the gas sensing space S and securely coupled to the holder 140.

The filter 150 may be expanded in the planar direction to cover the through hole of the holder 140, and may filter foreign substances contained in external gas introduced via the through hole.

The gas sensor according to the embodiment of the present disclosure has the holder 140 and the filter 150 that are located inside the gas sensing space S. Therefore, the gas sensor may prevent the foreign substances filtered by the filter 150 from penetrating into the gas sensing space S.

The housing 110 has a support 111 that is extended to protrude from a bottom surface at a periphery of the open portion O toward the circuit board 130. The holder 140 may be coupled to the support 111 while being spaced apart from the bottom surface at the periphery of the open portion O of the housing 110 toward the circuit board 130.

The support 111 may be extended from the bottom surface of the housing 110 toward the circuit board 130. The height of the support 111 may be appropriately set such that the holder 140 and the filter 150 are spaced apart from the bottom surface of the housing 110 and from the circuit board 130.

The holder 140 may be coupled to a protruding-extended end of the support 111.

Figure 4:
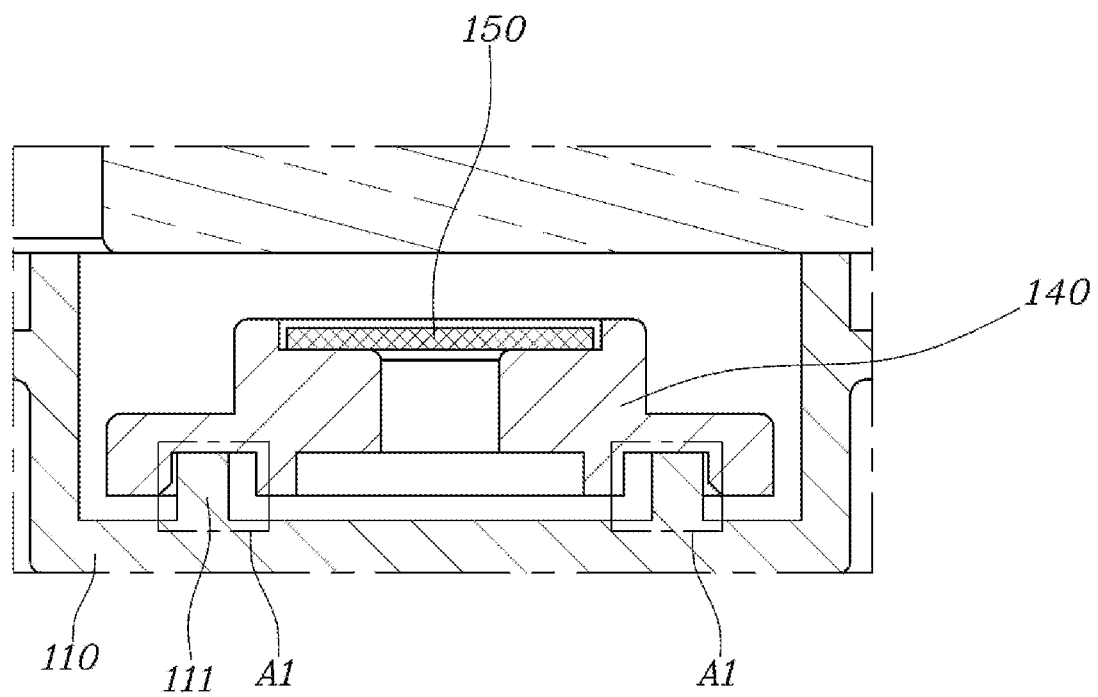
FIG. 4 is a view showing coupling between a holder and a support according to the embodiment of the present disclosure.

FIG. 4 is a view showing coupling between the holder 140 and the support 111 according to the embodiment of the present disclosure.

Referring to FIG. 4, as the embodiment, the holder 140 may be integrally coupled to the support 111 by being fused thereto by ultrasonic waves, lasers, vibration, or heat.

Specifically, one surface of the holder 140 may be fused to the support 11 by ultrasonic waves, lasers, vibration, or heat in a state A1 in which the surface of the holder 140 is in contact with the support 111. Accordingly, the holder 140 and the support 111 may be integrally coupled to each other by physical and chemical transformation.

The holder 140 may be expanded outward more than the support 111 and have an insertion groove 141 between an outer end 143 and an inner end 142 surrounding the through hole. The support 111 may be coupled to the holder 140 while being inserted in the insertion groove 141 between the outer end 143 and the inner end 142 of the holder 140.

As the holder 140 is expanded outward more than the support 111 surrounding the open portion O and extended to protrude from the bottom surface of the housing 110, the holder 140 may cover both the open portion O and the support 111 at the same time.

The holder 140 may have the insertion groove 141 at a location corresponding to the support 111. The insertion groove 141 may be depressed inward so that the end of the support 111 is inserted therein. Specifically, the insertion groove 141 may be formed between the outer end 143 and the inner end 142 that are respectively extended circumferentially and radially spaced apart from each other.

Figure 5:
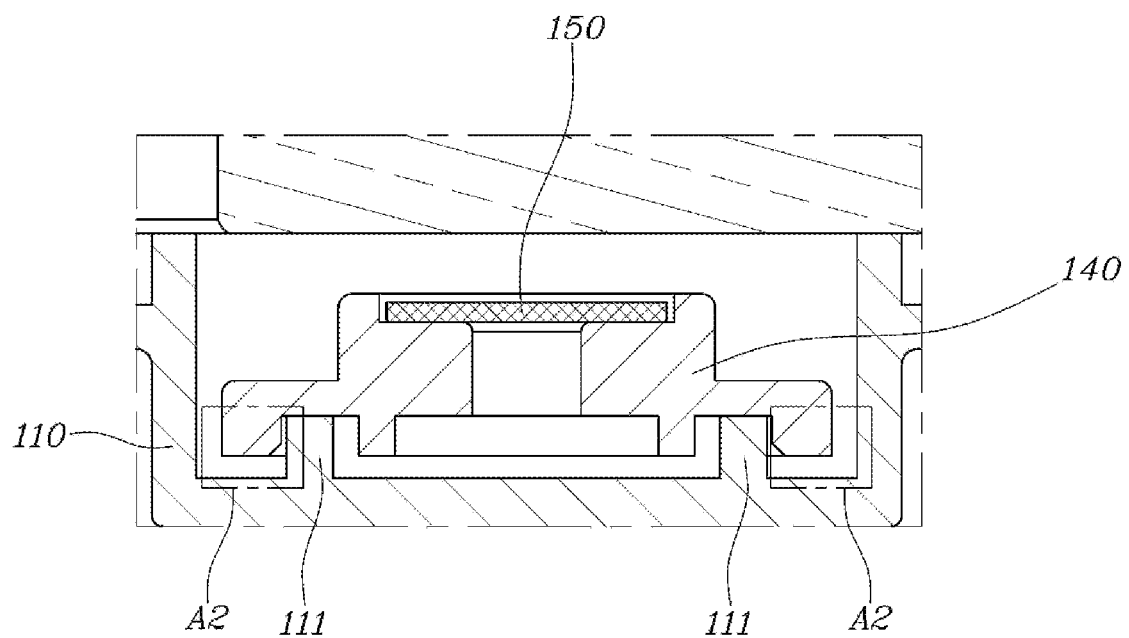
FIG. 5 is a view showing coupling between a holder and a support according to another embodiment of the present disclosure.

FIG. 5 is a view showing coupling between the holder 140 and the support 111 according to another embodiment of the present disclosure.

Referring to FIG. 5, an adhesive is applied on a portion A2 between the holder 140 and the bottom surface of the housing 110 that are spaced apart from each other according to the another embodiment of the present disclosure. The holder 140 may be integrally coupled to the housing 110 by the adhesive.

The adhesive may be applied on a space A2 between the outer end 143 surrounding the insertion groove 141 of the holder 140 from the outside of the insertion groove 141 and the bottom surface of the housing 110. Therefore, the housing 110 and the holder 140 may be coupled to each other by the adhesive without physical and chemical deformation.

As the embodiment, the adhesive may be a gel type or epoxy.

In addition, the adhesive may be applied on a portion between the holder 140 and the support 111.

Figure 6:
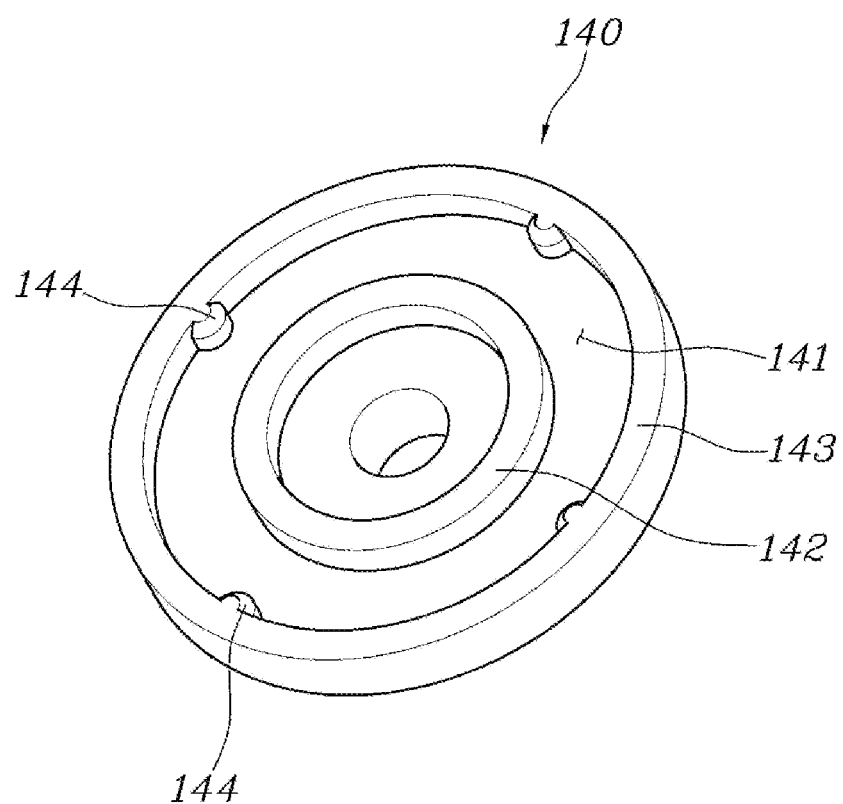
FIG. 6 is a perspective view showing the holder according to the embodiment of the present disclosure.

FIG. 6 is a perspective view showing the holder 140 according to the embodiment of the present disclosure.

Referring to FIG. 6, the holder 140 may have protrusions 144 formed at a plurality of locations on the outer end 143 or the inner end 142 and protruding toward the insertion groove 141. The locations are circumferentially spaced apart from each other. The support 111 may be fixed at its location inside the insertion groove 141 as the support 111 is in contact with the protrusions 144.

The insertion groove 141 of the holder 140 may be formed between the outer end 143 and the inner end 142 that are radially spaced apart from each other. The protrusions 144 of the holder 140 may protrude from the outer end 143 toward the inner end 142 or from the inner end 142 toward the outer end 143.

The protrusions 144 may be formed on the plurality of locations on the holder 140 which are circumferentially spaced apart from each other.

Therefore, as the protrusions 144 restrain the location of the support 111 inserted in the insertion groove 141 formed between the outer end 143 and the inner end 142 of the holder 140, a coupling location between the support 111 and the housing 110 may be fixed.

In addition, the minimum distance between each of the protrusions 144 and the inner end 142 or between the protrusion 144 and the outer end 143 may correspond to the thickness of the support 111.

Figure 7:
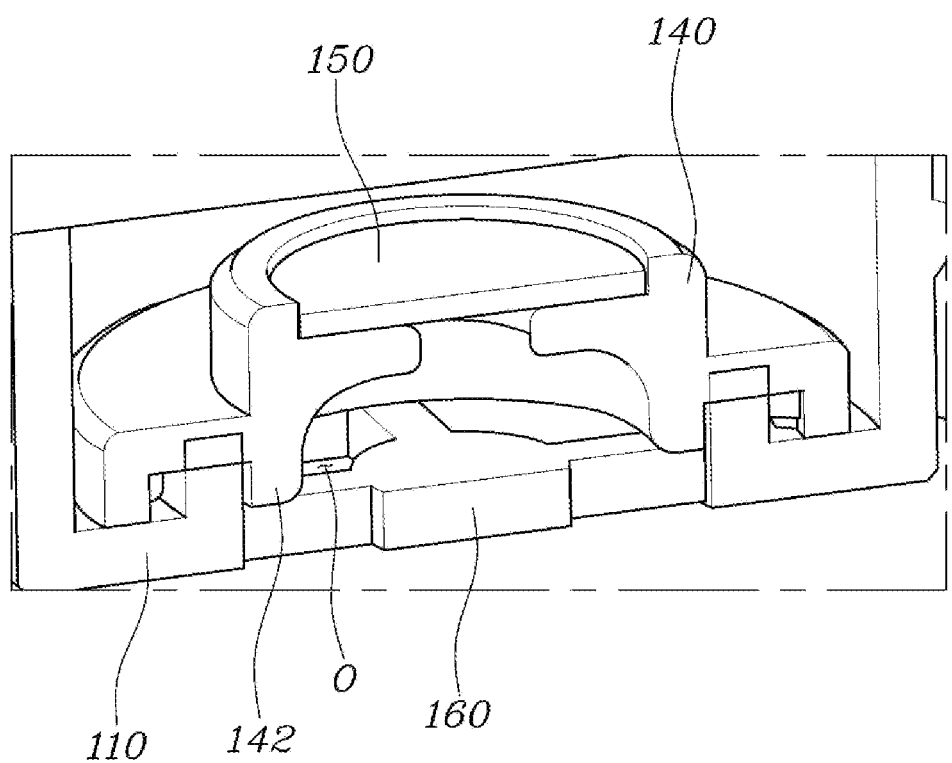
FIG. 7 is a perspective view showing the gas sensor according to the embodiment of the present disclosure.

FIG. 7 is a perspective view showing the gas sensor 100 according to the embodiment of the present disclosure.

Referring to FIG. 7, the holder 140 may have a curved surface such that the inner end 142 is gradually extended inward.

The through hole is extended on the center of the holder 140 and has a hollow through inside so as to communicate with the open portion O. The through hole may be extended toward the circuit board 130 and the gas sensing space S.

Among the outer end 143 and the inner end 142 of the holder 140 that define the insertion groove 141, the inner end 142 may be radially spaced apart from the through hole. The holder 140 may be extended between the inner end 142 and the through hole in a planar direction.

Specifically, an edge of the holder 140 on a flow path of the gas introduced into the through hole through the open portion O is rounded to form a curved surface as the holder is gradually extended inward from the inner end 142. Therefore, pressure drop and flow rate drop of gas caused in response to a flow of the gas from the open portion O to the through hole can be prevented.

Referring to FIGS. 2 to 3, the circuit board 130 is coupled to the housing 110 in a direction facing the open portion O. The circuit board 130 may be coupled to the housing 110 so as to maintain airtightness of the gas sensing space S from other space inside the housing 110.

The circuit board 130 is spaced apart from the bottom surface of the housing on which the open portion O is formed to provide the gas sensing space S. The circuit board 130 may be coupled to the housing 110 in a direction facing the bottom surface. Specifically, in order to maintain airtightness of the gas sensing space S from the other inside space of the housing 110, the housing 110 and the circuit board 130 may be coupled to each other.

The housing 110 may include a seating groove 112 and an elastic body 170. The seating groove 112 may be located outside the gas sensing space S and be depressed in a direction that is spaced apart from the circuit board 130, and the elastic body 170 may be located between the housing 110 and the circuit board 130 and be disposed inside the seating groove 112.

As the embodiment, the elastic body 170 may be an O-ring. The elastic body 170 may be inserted into the seating groove 112 while being located between the housing 110 and the circuit board 130. Specifically, the seating groove 112 may be located outside the gas sensing space S and may surround the gas sensing space S at a position outside the gas sensing space S.

Accordingly, even when an assembly tolerance or a tolerance between the housing 110 and the circuit board 130 occurs or the gas sensor is partially deformed by an impact, stress is not applied on the circuit board 130, and leakage of gas flowing into the gas sensing space S may be prevented.

The filter 150 may be expanded outward more than the through hole to cover the through hole, and may be coupled to the holder 140 at the side opposite to the open portion O.

The filter 150 may filter foreign substances contained in the gas introduced via the through hole. The filter 150 may be coupled to the holder 140 at the side opposite to the open portion O so as to be located inside the gas sensing space S. Furthermore, the filter 150 may be expanded outward more than the through hole so as to cover the entire through hole. Accordingly, gas not filtered by the filter 150 may not be introduced into the through hole.

The filter 150 may be integrally coupled to the holder 140 or the housing 110 by being fused thereto by ultrasonic waves, lasers, vibration, or heat while being spaced apart from the circuit board 130.

Referring to FIG. 2, a guide member 160 may be fixed to the housing 110. The guide member 160 may be extended in a direction perpendicular to a penetrating direction of the through hole to cover the through hole, at the open portion O, in the penetrating direction of the through hole.

The guide member 160 may be fixed to the housing 110 and block part of the open portion O. As the embodiment, the guide member 160 may be formed in a shape corresponding to a shape of the through hole. When a section of the through hole is a circular shape, the guide member 160 may also be formed in the circular shape.

As the embodiment, the guide member 160 is extended from the center of the open portion O outward more than the through hole. The gas introduced into the open portion O may be introduced through an outer area of the guide member 160 while avoiding the guide member 160. The gas may be covered by the guide member 160 and be introduced into the through hole.

The guide member 160 may primarily block foreign substances flowing via the open portion O and guide a gas flow direction for the gas to flow into the through hole.

The guide member 160 may be extended outward at a plurality of portions of the guide member 160, which are circumferentially spaced apart from each other, and each extended end may be fixed to the housing 110.

The guide member 160 may be formed in a circular shape with a radius (R) that is equal to or longer than a distance L1 between the through hole and the guide member 160 and is shorter than or equal to a distance L2 between the filter 150 and the guide member 160.

Specifically, the guide member 160 may be extended outward more than the through hole and thus be formed larger than the size of the through hole. Accordingly, the guide member 160 may block foreign substances including moisture flowing via the open portion O from the front of the open portion O.

Furthermore, the guide member 160 may be formed in a circular shape with a radius R that is equal to or longer than a distance L1 between the holder 140 and the guide member 160 or the through hole of the holder 140 and the guide member 160. The radius R of the guide member 160 may be formed longer than the distance L1 between the guide member 160 and the through hole. Accordingly, the guide member 160 may primarily block moisture flowing into the through hole from the open portion O.

Furthermore, the guide member 160 may be formed in a circular shape with a radius R that is shorter than or equal to the distance L2 between the filter 150 fixed to the holder 140 and the guide member 160. Therefore, the guide member 160 may prevent the filter 150 from separation from the holder 140 due to external water pressure.

Figure 8:
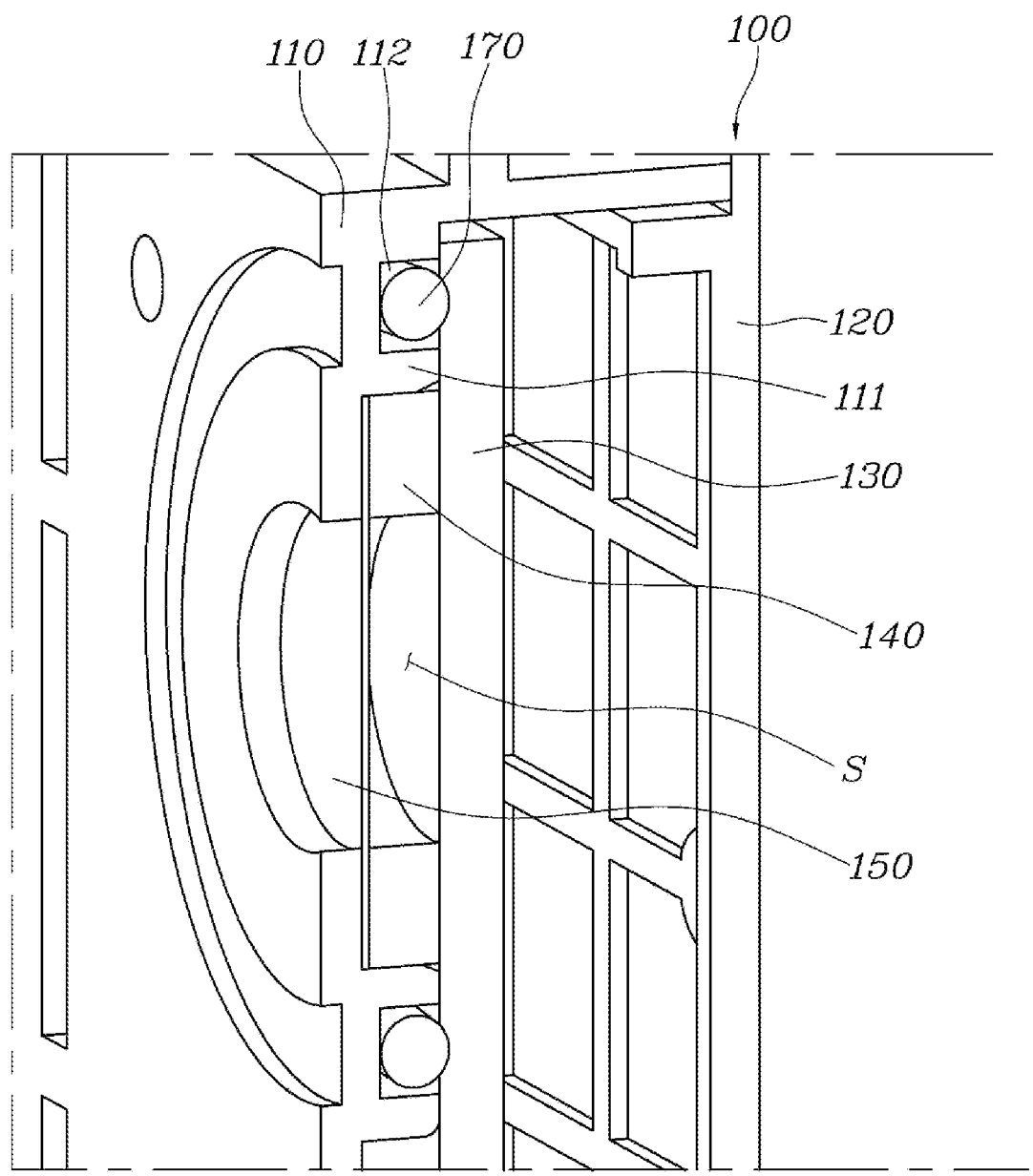
FIG. 8 is a perspective view showing the gas sensor in a cut away state according to the another embodiment of the present disclosure.

FIG. 8 is a perspective view showing the gas sensor 100 in a cut away state according to the another embodiment of the present disclosure.

Referring to FIG. 8, the filter 150 of the gas sensor 100 according to the another embodiment of the present disclosure may be provided between the housing 110 and the holder 140 and cover both the open portion O and the through hole at the same time. The filter 150 may be spaced apart from the circuit board 130 and may define the gas sensing space S.

Specifically, as the filter 150 is directly coupled to the housing 110 or is disposed between the holder 140 coupled to the housing 110 and the housing 110, separation of the filter 150 may be prevented and the filter 150 may be fixed to the housing 110 or the holder 140.

The filter 150 may cover the open portion O while being in directly contact with the housing 110. The filter 150 may define the gas sensing space S by being spaced apart from the circuit board 130 with the holder 140 located between the filter 150 and the circuit board 130.

The housing 110 may have the support 111 extended to protrude from the bottom surface of the periphery of the open portion O toward the circuit board 130. The holder 140 may be fixed to the housing 110 while being inserted in the support 111.

The holder 140 may be inserted into the support 111 so that a part of or the entire outer end of the holder is in contact with an inner circumferential surface of the support 111. The holder 140 may be coupled to the support 111 or the housing 110 while being inserted in the support 111.

As the embodiment, the holder 140 may be expanded outward such that, a part of or the entire outer end of the holder 140 may be expanded outward more than the inner circumferential surface of the support 111. The holder 140 may be integrally coupled to the support 111 in a forced insertion manner.

The outer end of the holder 140 may be a cylinder with a smooth surface. The holder 140 may have an outer diameter larger than the inner circumferential surface of the support 111, so that the entire outer end of the holder 140 may be expanded outward more than the inner circumferential surface of the support 111. As the holder 140 is inserted into the support 111, the support 111 may be elastically deformed to prevent separation of the holder 140.

Figure 9:
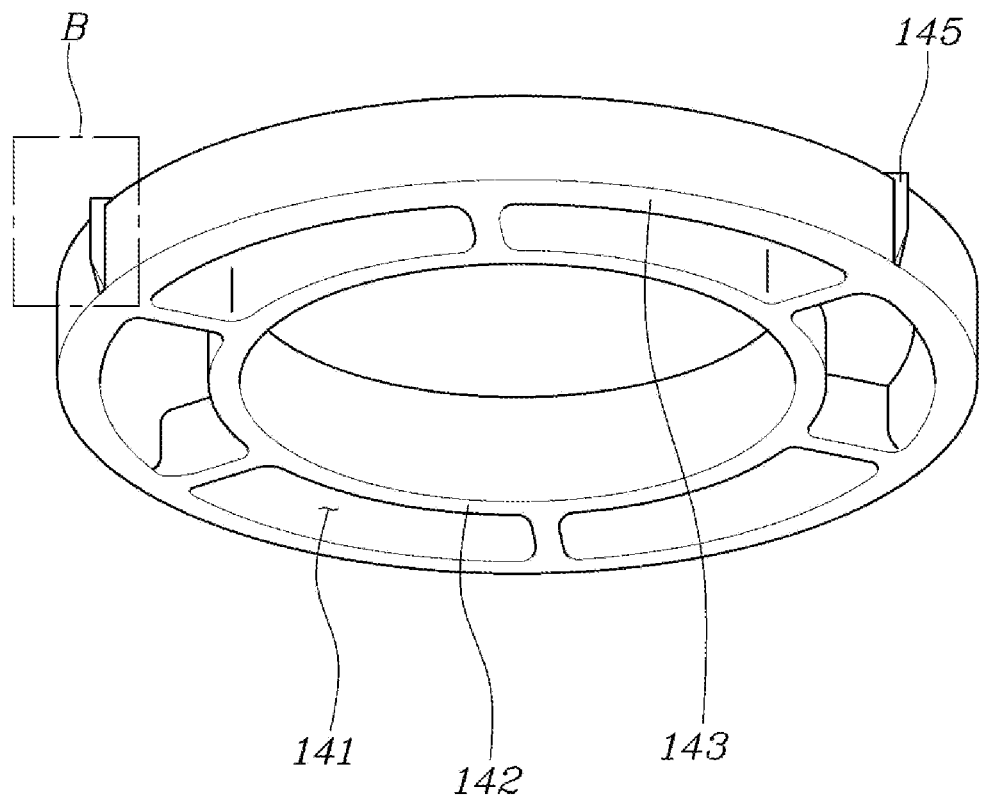
FIG. 9 is a perspective view showing the holder according to the another embodiment of the present disclosure.
Figure 10:
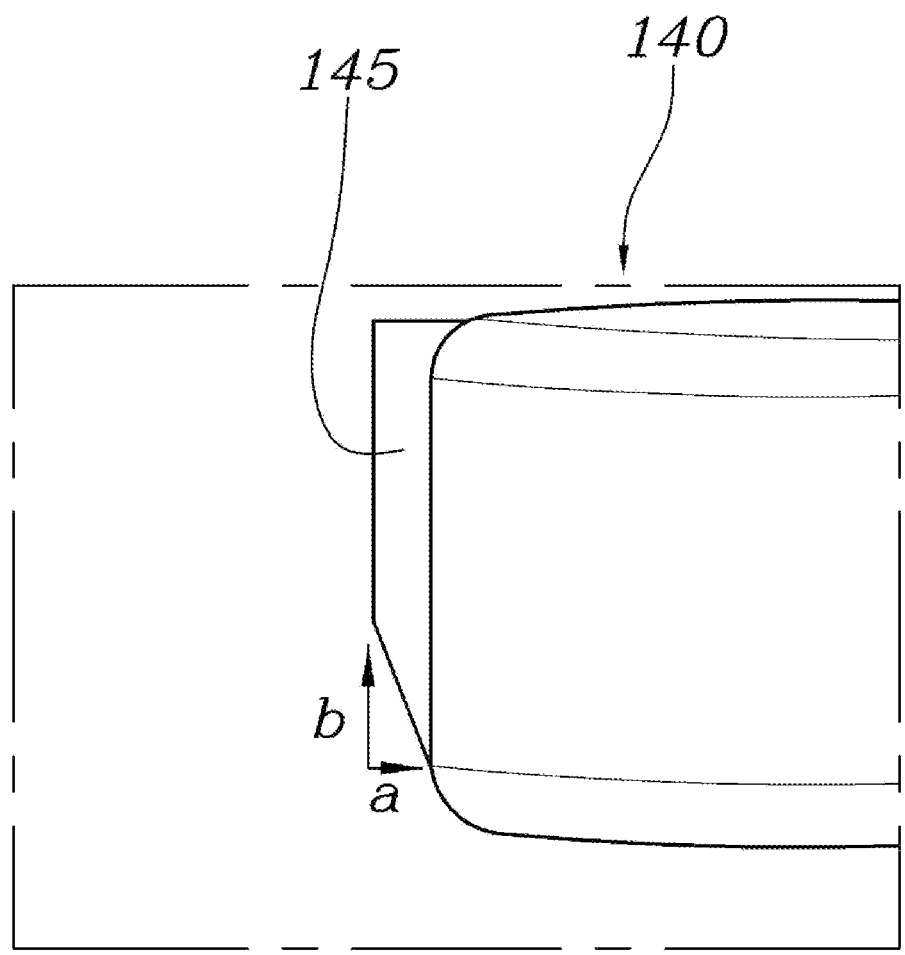
FIGS. 10 and 11 are a front view and a top view showing an enlarged area B in FIG. 9.
Figure 11:
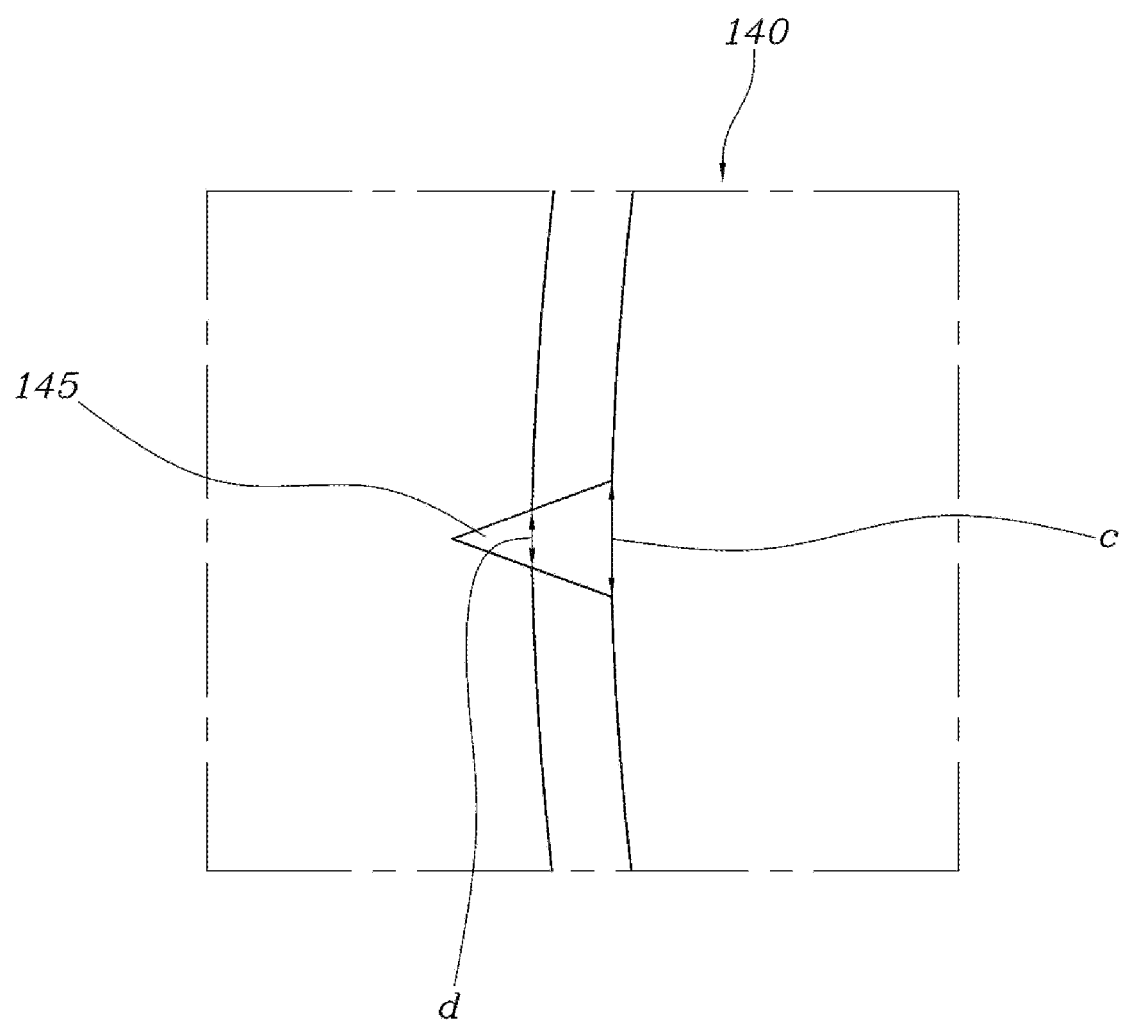

FIG. 9 is a perspective view showing the holder 140 according to the another embodiment of the present disclosure. FIGS. 10 and 11 are a front view and a top view showing an enlarged area B in FIG. 9.

Referring to FIGS. 9 to 11, as the another embodiment, the holder 140 may have an inclined protrusion 145. The inclined protrusion 145 may protrude outward from at least one location on the outer end of the holder 140. The inclined protrusion 145 may be deformed while being inserted into the support 111.

As the inclined protrusion 145 is inserted into the support 111 and is pressurized on the inner circumferential surface of the support 111, the inclined protrusion 145 may be elastically or plastically deformed, and thus be fixed to the support 111.

The inclined protrusion 145 may be inclined such that the height of the inclined protrusion 145 is lowered as the inclined protrusion 145 goes in an inserted direction into the support 111, or be inclined such that the width of the inclined protrusion 145 narrows as the inclined protrusion is extended outward.

As shown in FIG. 10, the inclined protrusion 145 may be inclined such that the height (a) of the inclined protrusion 145 is lowered as the inclined protrusion goes in the inserted direction into the support 111. Specifically, the inclined length (b) of the inclined protrusion 145 is formed longer than the height (a) of the inclined protrusion 145, so that the inclined protrusion 145 may be gradually inclined in the inserted direction into the support 111.

As shown in FIG. 11, the inclined protrusion 145 may be inclined such that the width of the inclined protrusion 145 narrows as the inclined protrusion 145 is extended outward. Specifically, the inclined protrusion 145 may be formed such that an outer width (d) of the inclined protrusion 145 extended outward is smaller than an inner width (c) of the inclined protrusion 145 located close to the outer end of the holder 140.

Figure 12:
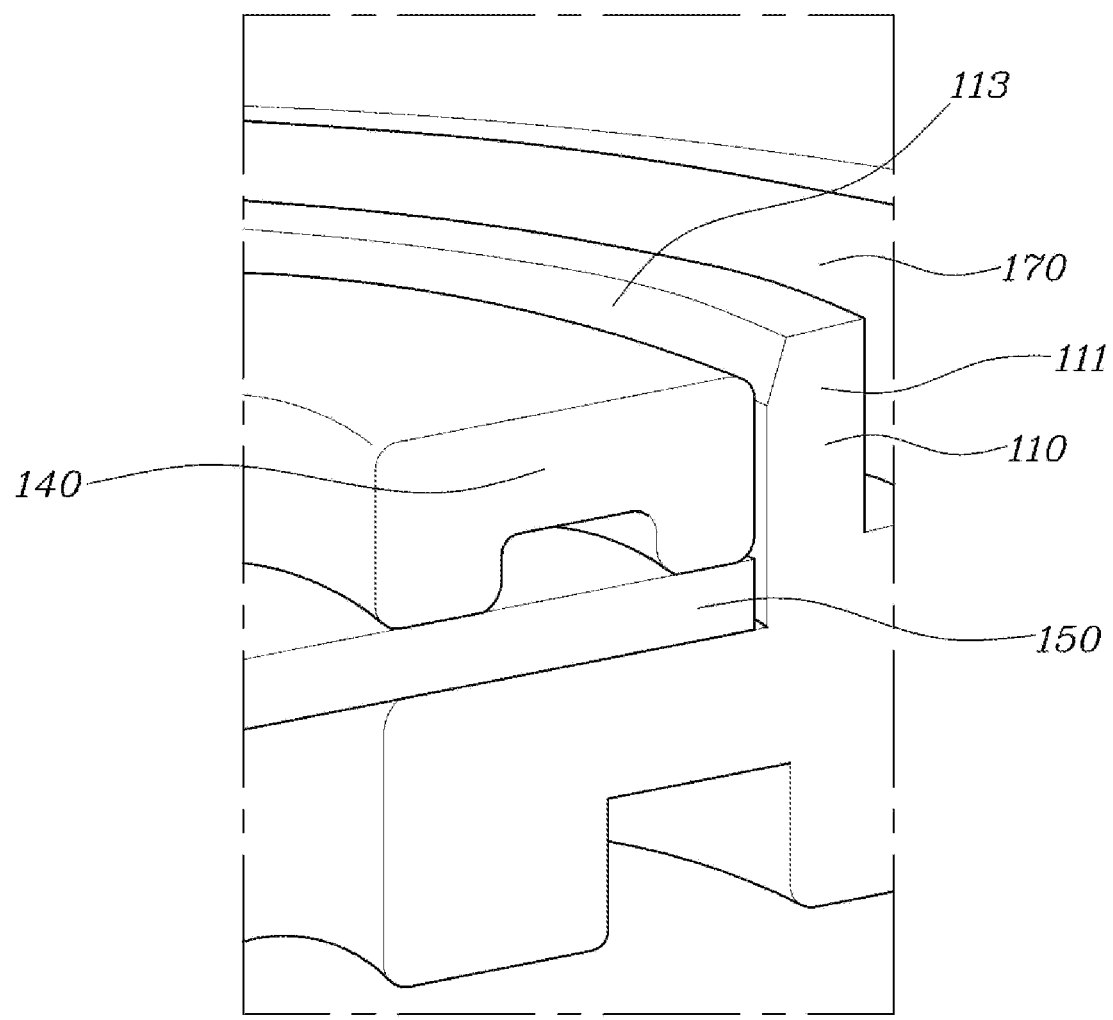
FIG. 12 is a perspective view showing the gas sensor in a cut away state according to the another embodiment of the present disclosure.
Figure 13:
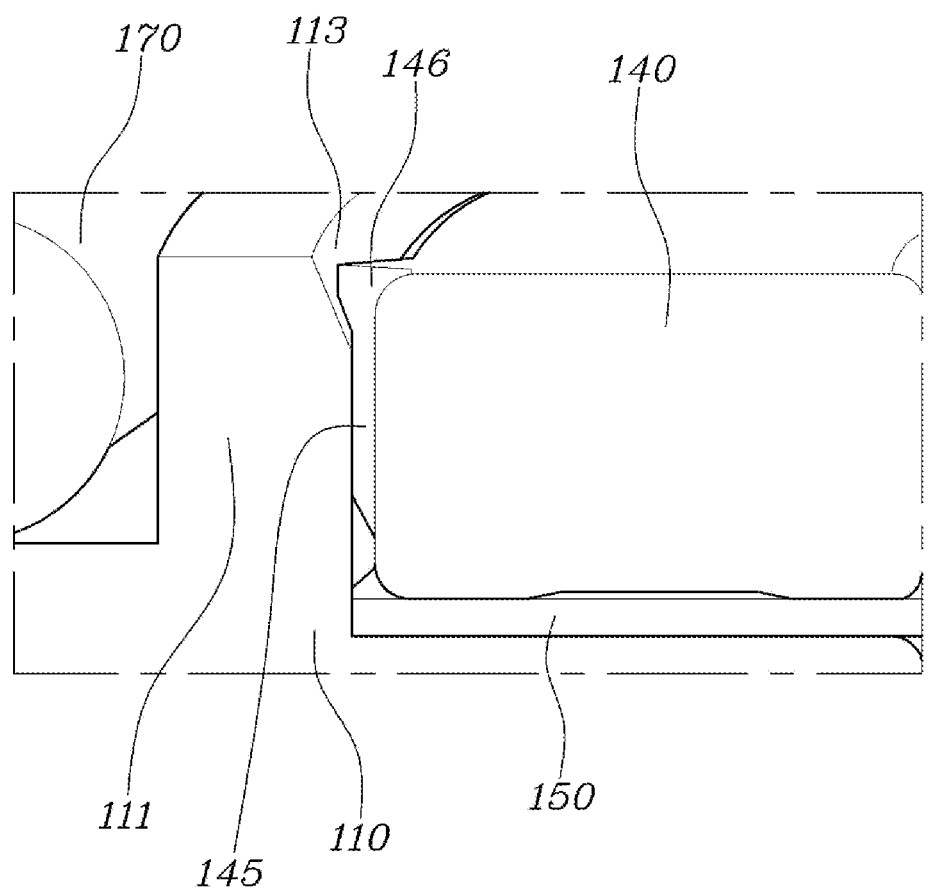
FIG. 13 is a sectional view showing the gas sensor in a cut away state according to the another embodiment of the present disclosure.

FIG. 12 is a perspective view showing the gas sensor 100 in a cut away state according to the another embodiment of the present disclosure. FIG. 13 is a sectional view showing the gas sensor 100 in a cut away state according to the another embodiment of the present disclosure.

Referring to FIGS. 12 and 13, the support 111 may be thermally deformed while accommodating the holder 140 therein and thus be integrally coupled to the holder 140.

After the holder 140 is inserted into the support 111, the support 111 or the holder 140 may be thermally deformed in the inserted direction of the holder 140. For example, a space between the outer end of the holder 140 and the inner circumferential surface of the support 111 may be filled with the support 111 or the holder 140 that is deformed by a heat stacking method.

As the embodiment, the support 111 may be extended such that an end 113 of at the circuit board side is higher than the holder 140 while the holder 140 is inserted in the support 111. The space between the outer end of the holder 140 and the inner circumferential surface of the support 111 may be filled as the support 111 is thermally deformed while the holder 140 is inserted in the support 111.

Specifically, the support 111 is extended higher than the height of the holder 140, and an inner circumferential surface of the end 113 at the circuit board side is depressed to be inclined outward as the end 113 at the circuit board side directs toward the circuit board 130. Therefore, the support 111 may be thermally deformed inward.

In other words, the end 113 at the circuit board side, which is depressed to be inclined outward as the end of the support 111 is extended, may be thermally deformed along the inclination of the end 113 toward the outer end of the holder 140 located at a relatively lower side.

In addition, the inclined protrusion 145 may protrude outward to correspond to the end 113 at the circuit board side of the support 111. An end 146 at the circuit board side of the inclined protrusion 145 may be extended outward as the inclined protrusion 145 directs toward the circuit board 130.

The gas sensor according to the embodiment of the present disclosure may be applied to a fuel cell system at various locations.

The gas sensor 100 according to the embodiment of the present disclosure senses hydrogen leakage. The gas sensor 100 may be a gas sensor configured to sense a hydrogen concentration range within 0~4%.

As the embodiment, the gas sensor 100 according to the present disclosure may be included at anode of a fuel cell stack.

A valve may be located between a hydrogen tank and a hydrogen supply line in the fuel cell system. The gas sensor 100 according to the embodiment of the present disclosure may be located between the hydrogen tank and the valve or between the valve and an ejector.

Accordingly, the gas sensor 100 according to the embodiment of the present disclosure may sense hydrogen leakage occurring between the hydrogen tank and the valve or hydrogen leakage occurring between the valve and the ejector.

Although the preferred embodiment of the present disclosure has been described for illustrative purposes, those skilled in the art will appreciate that various modifications, additions and substitutions are possible, without departing from the scope and spirit of the disclosure as disclosed in the accompanying claims.

What is claimed is:

1. A gas sensor, comprising:
a housing having an open portion at one side of the housing;
a circuit board securely provided inside the housing, the circuit board defining a gas sensing space in the housing that communicates with the open portion of the housing, and the circuit board having a sensing element located in the gas sensing space and configured to sense a specific gas;
a holder provided inside the gas sensing space, and fixed to the housing, the holder having a through hole communicating with the open portion of the housing; and
a filter provided inside the gas sensing space, and coupled to the holder or the housing so as to cover the through hole or the open portion,
wherein the circuit board is coupled to the housing while facing the open portion of the housing, so that the gas sensing space is maintained airtight from an inside space of the housing, and
wherein the housing has a seating groove located outside the gas sensing space and depressed in a direction that is spaced apart from the circuit board, the housing further comprising an elastic body located between the housing and the circuit board and disposed in the seating groove.

2. The gas sensor of claim 1, wherein the housing comprises a support that is extended to protrude from a bottom surface at a periphery of the open portion of the housing toward the circuit board, and
the holder is coupled to the support while being spaced apart from the bottom surface at the periphery of the open portion of the housing toward the circuit board.

3. The gas sensor of claim 2, wherein the holder is integrally coupled to the support by being fused thereto by ultrasonic waves, lasers, vibration, or heat.

4. The gas sensor of claim 2, wherein:
the holder is expanded outward more than the support,
the holder has an insertion groove at a portion between an outer end and an inner end of the holder surrounding the through hole, and
the support is coupled to the holder while being located between the outer end and the inner end of the holder and being inserted in the insertion groove.

5. The gas sensor of claim 4, wherein the holder has protrusions, the protrusions being formed on a plurality of locations on the outer end or the inner end of the holder and protruding toward the insertion groove and being circumferentially spaced apart from each other, and
the support is fixed at a location inside the insertion groove by being in contact with the protrusions.

6. The gas sensor of claim 4, wherein the holder has a curved surface as the inner end of the holder is gradually extended inward.

7. The gas sensor of claim 2, wherein an adhesive is applied on a portion between the holder and the bottom surface in the housing that are spaced apart from each other, and the holder is integrally coupled to the housing by the adhesive.

8. The gas sensor of claim 1, wherein the filter is expanded outward more than the through hole to cover the through hole and is coupled to the holder at a side opposite to the open portion of the housing.

9. The gas sensor of claim 1, wherein the filter is integrally coupled to the holder or the housing by being fused thereto by ultrasonic waves, lasers, vibration, or heat while being spaced apart from the circuit board.

10. The gas sensor of claim 1, wherein a guide member is fixed to the housing, the guide member being extended in a direction perpendicular to a penetrating direction of the through hole to cover the through hole, at the open portion, in the penetrating direction of the through hole.

11. The gas sensor of claim 10, wherein the guide member has a circular shape with a radius that is equal to or longer than a distance between the guide member and the through hole and is shorter than or equal to a distance between the guide member and the filter.

12. The gas sensor of claim 1, wherein the filter is provided between the housing and the holder and covers both the open portion of the housing and the through hole at the same time, the filter defining the gas sensing space while being spaced apart from the circuit board.

13. The gas sensor of claim 12, wherein the housing comprises a support that is extended to protrude from a bottom surface at a periphery of the open portion toward the circuit board, and
the holder is fixed to the housing while being inserted in the support.

14. The gas sensor of claim 13, wherein the holder is extended outward such that, a part of or an entire outer end of the holder is extended outward more than an inner circumferential surface of the support, the holder being integrally coupled to the support by a forced insertion manner.

15. The gas sensor of claim 13, wherein the holder has an inclined protrusion, the inclined protrusion protruding outward from at least one location on an outer end of the holder and being configured to be deformed while being inserted into the support.

16. The gas sensor of claim 15, wherein the inclined protrusion is inclined such that a height of the inclined protrusion is lowered as the inclined protrusion goes in an inserted direction into the support, or is inclined such that a width of the inclined protrusion narrows as the inclined protrusion is extended outward.

17. The gas sensor of claim 13, wherein the support is configured to be thermally deformed while accommodating the holder therein and thus be integrally coupled to the holder.

18. The gas sensor of claim 17, wherein the support is extended higher than a height of the holder, and as an end at the circuit board side of the support is directed toward the circuit board, an inner circumferential surface of the support is depressed to be inclined outward, so that the support is thermally deformed inward.

19. A gas sensor, comprising:
a housing having an open portion at one side of the housing;
a circuit board securely provided inside the housing, the circuit board defining a gas sensing space in the housing that communicates with the open portion of the housing, and the circuit board having a sensing element located in the gas sensing space and configured to sense a specific gas;
a holder provided inside the gas sensing space, and fixed to the housing, the holder having a through hole communicating with the open portion of the housing; and
a filter provided inside the gas sensing space, and coupled to the holder or the housing so as to cover the through hole or the open portion,
wherein the filter is provided between the housing and the holder and covers both the open portion of the housing and the through hole at the same time, the filter defining the gas sensing space while being spaced apart from the circuit board,
wherein the housing comprises a support that is extended to protrude from a bottom surface at a periphery of the open portion toward the circuit board, and
wherein the holder is fixed to the housing while being inserted in the support.

* * * * *